US009259285B2

(12) United States Patent
Dunn

(10) Patent No.: US 9,259,285 B2
(45) Date of Patent: Feb. 16, 2016

(54) SCRUB FOR INHIBITING CATHETER ASSOCIATED URINARY TRACT INFECTIONS

(71) Applicant: Susan V. Dunn, Carmel, IN (US)

(72) Inventor: Susan V. Dunn, Carmel, IN (US)

( * ) Notice: Subject to any disclaimer, the term of this patent is extended or adjusted under 35 U.S.C. 154(b) by 38 days.

(21) Appl. No.: 14/453,163

(22) Filed: Aug. 6, 2014

(65) Prior Publication Data

US 2015/0040943 A1  Feb. 12, 2015

Related U.S. Application Data

(60) Provisional application No. 61/912,331, filed on Dec. 5, 2013, provisional application No. 61/862,636, filed on Aug. 6, 2013.

(51) Int. Cl.
| | |
|---|---|
| *B08B 7/00* | (2006.01) |
| *A61B 19/00* | (2006.01) |
| *A61F 13/40* | (2006.01) |
| *B08B 1/00* | (2006.01) |
| *A47L 13/24* | (2006.01) |
| *A61C 19/00* | (2006.01) |
| *A47L 13/16* | (2006.01) |
| *A47L 13/26* | (2006.01) |

(52) U.S. Cl.
CPC .............. *A61B 19/36* (2013.01); *A61M 35/006* (2013.01); *A47L 13/16* (2013.01); *A47L 13/24* (2013.01); *A47L 13/26* (2013.01); *A61B 19/34* (2013.01); *A61B 19/38* (2013.01); *A61C 19/002* (2013.01); *B08B 1/00* (2013.01); *B08B 1/003* (2013.01)

(58) Field of Classification Search
CPC ........ A61B 19/36; A61B 19/38; A61B 19/34; A61M 35/006; A61C 19/002; A47L 13/16; A47L 13/26; B08B 1/00; B08B 1/003
See application file for complete search history.

(56) References Cited

U.S. PATENT DOCUMENTS

| | | |
|---|---|---|
| 4,710,169 A | 12/1987 | Christopher |
| 4,723,946 A | 2/1988 | Kay |
| 5,207,652 A | 5/1993 | Kay |
| 5,263,947 A | 11/1993 | Kay |

(Continued)

FOREIGN PATENT DOCUMENTS

CN   201978329   9/2011

OTHER PUBLICATIONS

System Cauti Prevention Team (Sharp Grossmont Hospital): "Catheter Associated Urinary Tract Infection (CAUTI) Prevention" Brochure—2009—La Mesa CA 91942.
Pediatric Erase CAUTI (Foley Catheter); www.GoSouthernMD.com May 27, 2013.
Silvertouch Foley Catheter www.medline.com May 28, 2013.

*Primary Examiner* — Bibi Carrillo
(74) *Attorney, Agent, or Firm* — Overhauser Law Offices LLC

(57) ABSTRACT

A one time use cleansing device for inhibiting catheter associated urinary tract infections. An absorbent body includes a plurality of fingerlings extending outwardly from a front side of the absorbent body. First and second wings extend from a back side of the absorbent body. One or more liquid containing frangible vials are disposed between the first and second wings such that squeezing the wings together causes the vials to rupture, thereby releasing the contents of the vials into the absorbent body. The absorbent body and/or the one or more vials contain a cleansing agent of castile soap and tea tree oil designed to aid in the inhibition and/or prevention of catheter associated urinary tract infections (CAUTIs).

11 Claims, 3 Drawing Sheets

(56) References Cited

U.S. PATENT DOCUMENTS

| | | | |
|---|---|---|---|
| 5,368,575 A | 11/1994 | Chang | |
| 5,505,717 A | 4/1996 | Moore | |
| 5,593,389 A | 1/1997 | Chang | |
| 5,620,424 A | 4/1997 | Abramson | |
| 6,368,317 B2 | 4/2002 | Chang | |
| 2007/0161949 A1* | 7/2007 | Knox | A61M 25/0017 604/93.01 |
| 2013/0030415 A1 | 1/2013 | Britt | |
| 2014/0316380 A1* | 10/2014 | Davis | A61M 1/3653 604/508 |
| 2015/0040943 A1* | 2/2015 | Dunn | A61B 19/36 134/6 |

\* cited by examiner

SCRUB FOR INHIBITING CATHETER ASSOCIATED URINARY TRACT INFECTIONS

CROSS REFERENCE TO RELATED APPLICATIONS

This application claims the benefit of U.S. Provisional Applications 61/912,331 filed Dec. 5, 2013 and 61/862,636 filed Aug. 6, 2013, the disclosures of which are incorporated by reference.

FIELD OF THE INVENTION

The present invention relates to catheter care post insertion into a patient and, more particularly, to methods and devices for addressing catheter associated urinary tract infections.

BACKGROUND

Catheters are routinely used during medical care. In many instances, catheters remain in the patient for extended periods of time. When a catheter remains in a patient for an extended period of time, the risk of infection becomes a concern. Particularly, with the use of in-dwelling catheters such as Foley catheters, bacteria gains easier access to the body via the catheter insertion into the bladder. Overgrowth of bacteria can colonize in the bladder and infection can occur, increasing hospital stay, cost and morbidity of patients.

Catheter associated urinary tract infections (CAUTI's) are thus a serious concern. CAUTI's are the most common type of nosocomial infection, accounting for 40% of all nosocomial infections, with over 1 million cases reportedly annually. The cost for CAUTI medical intervention is estimated above 451 million dollars annually in the United States alone.

It is therefore very important to cleanse the catheter and the catheter (perineal) area to decrease the number of bacteria around the catheter insertion in order to reduce the likelihood of contracting a CAUTI.

Today, the daily bath process in many hospitals involves the use of chlorexidine or similar wipes instead of soap and water. Chlorexidine wipes are antibacterial wipes that are used over all of a patient's body. However, chlorexidine or similar wipes are not suitable for the perineal area and thus the catheter insertion area as they are too harsh for the mucosal tissues in this region of the body.

In view of the above, what is therefore needed is a manner of cleansing a catheter insertion area in order to help prevent catheter associated urinary tract infections.

SUMMARY OF THE INVENTION

Disclosed herein is a device and method for one-time use cleansing of a catheter insertion area as well as the perineal area of a person for inhibiting catheter associated urinary tract infections (CAUTIs).

In one form, the present CAUTI inhibiting device is a scrub having a sponge or sponge-like body imbued with a dehydrated cleansing solution of tea tree oil and castile soap. One or more frangible (e.g. glass) ampoules, vials or the like of sterile water (e.g. distilled water) are retained in a semi-rigid but pliable portion of a housing on the sponge body. A filter or screen is disposed between the vial(s) and the sponge body in order to prevent glass or other ruptured vial material from entering into the sponge body. The housing includes two wings formed of a generally rigid material that are connected by struts to sides of the portion of the housing holding the vial(s). Squeezing the wings together causes the struts to press against the portion of the housing surrounding the vial(s), thereby rupturing the vial(s). The sterile water is then absorbed by the sponge, hydrating the dehydrated cleansing solution. The sponge body includes a plurality of fingers or fingerlings that aid in dispersing the cleansing agent about the body and in cleaning of the desired area. Alternatively, the cleansing agent can be provided in the vials so as to be dispersed into the sponge when the vials are broken.

Use of the present CAUTI inhibiting scrub is a simple process. First, the scrub is removed from a sterile packaging or wrapper. The scrub is grasped by its wings and squeezed together. This ruptures the vial(s) thereby dispensing the liquid into the sponge, which serves to hydrate the dehydrated cleansing solution already within the sponge and/or disperse the cleansing solution contained in the vial(s) into the sponge. The scrub is now ready for one time use. The scrub is sized to allow cleaning of the desired area with one or more swipes, thereby reducing the chance that bacteria existing at the desired cleaning area remains. Moreover, the sponge fingers allow thorough cleaning of the desired area.

The castile and tea tree oil soap cleansing agent is mild, non-irritating to the skin and antibacterial, particularly with respect to bacteria known to cause CAUTIs.

The present CAUTI inhibiting scrub is the perfect solution to cleanse the catheter insertion and perineal area to aid in CAUTI prevention. The present CAUTI inhibiting scrub is also easy to manipulate with one hand.

DETAILED DESCRIPTION

Figure 1:
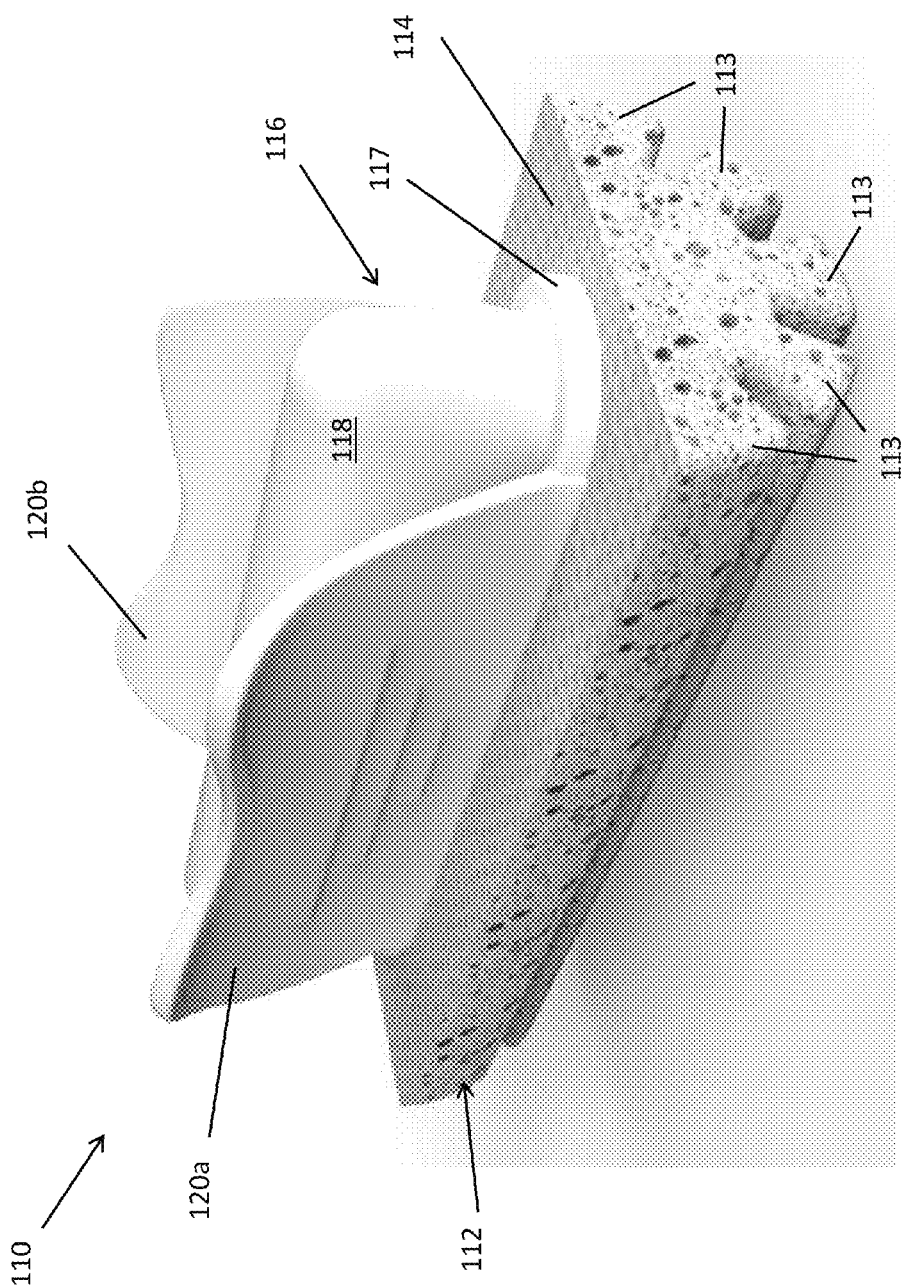
FIG. 1 is a front perspective view of an embodiment of a scrub for inhibiting CAUTIs fashioned in accordance with the present principles.
Figure 2:
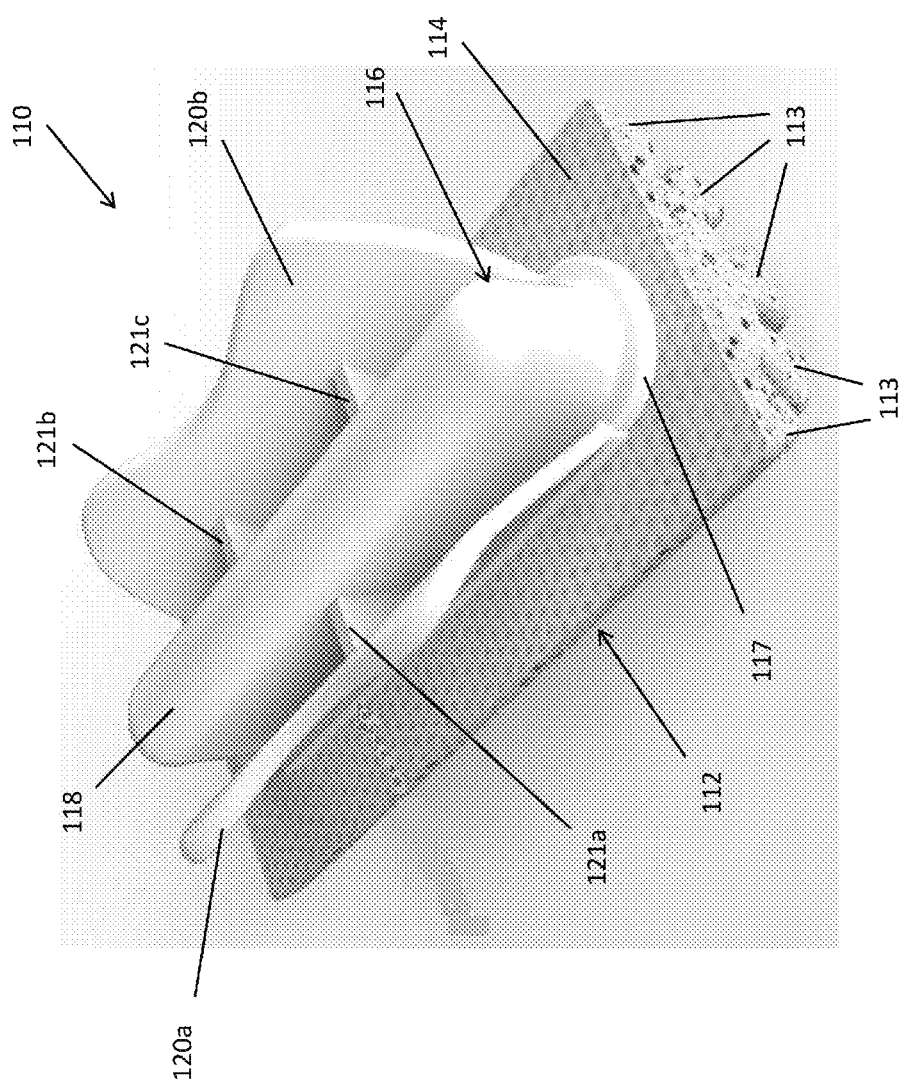
FIG. 2 is a top side perspective view of the CAUTI inhibition scrub of FIG. 1.
Figure 3:
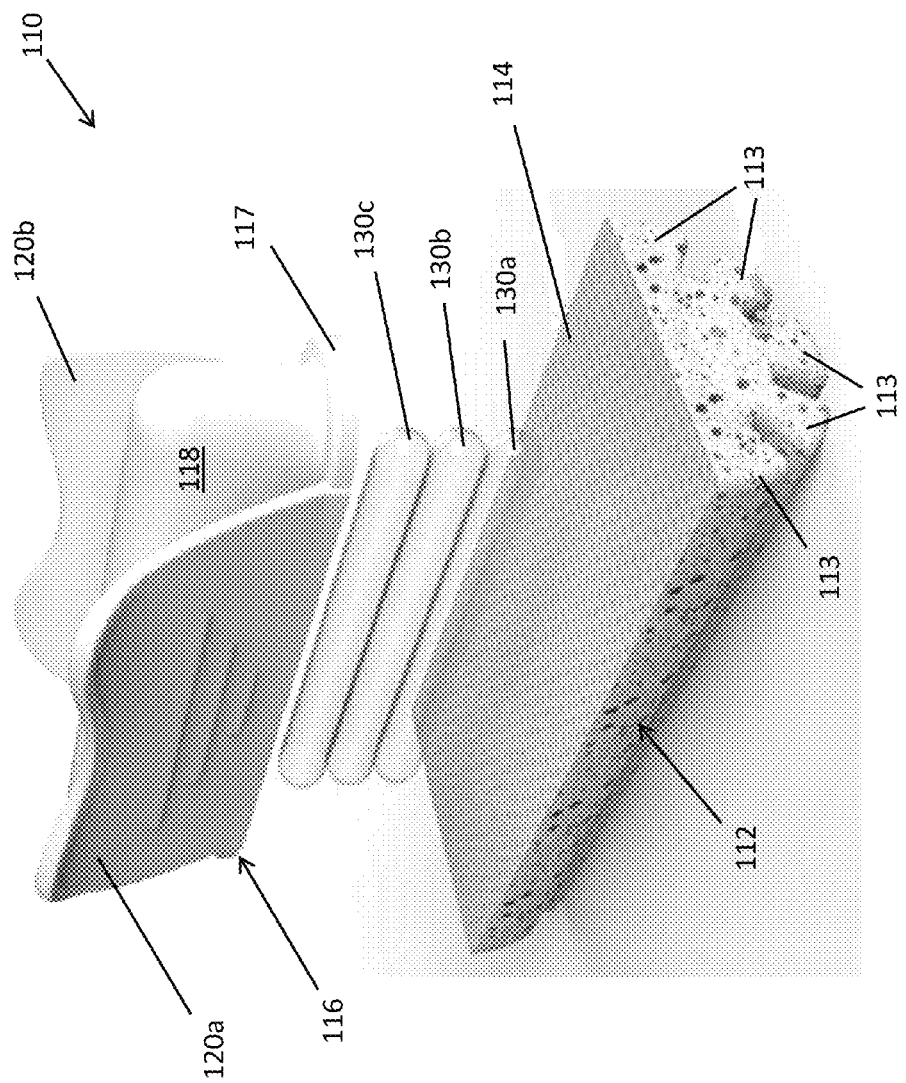
FIG. 3 is an exploded view of the CAUTI inhibition scrub of FIGS. 1 and 2.

Referring to the figures, there is depicted an exemplary embodiment of a device for inhibiting catheter associated urinary tract infections (CAUTIs) or CAUTI inhibiting scrub, generally designated 110, for cleansing an area of a person at and proximate to an indwelling catheter insertion site, in order to aid in the inhibition and/or prevention of a CAUTI. The indwelling catheter is typically, but not necessarily, a Foley catheter. The CAUTI inhibiting scrub 110 is characterized by a sponge or sponge-like body 112.

The body 112 preferably, but not necessarily, has an oblong rectangular shape that is sized to fit into one's hand. A plurality of fingers or fingerlings 113 extend along a bottom portion of the body 112 from one end to another end thereof. The fingers 113 are spaced from one another to form channels between the fingers. The body 112 is sized to provide enough surface area to completely clean the meatus area (catheter insertion area or perineal area) in one or more swipes, and preferably one swipe such that there is no need for repeated back and forth scrubbing or rubbing of the area. This inhibits spreading of any existing bacteria around the area.

The body 112 has a generally planar upper surface opposite the fingers 113. A filter, screen or the like 114 is situated on the upper surface of the sponge 112. The filter 114 may be situated over the entire upper surface (as shown) or just under the rim 117 of the housing 116. The filter 114 is configured to prevent debris such as glass or other material from a ruptured vial from entering into the sponge.

The housing 116 includes a housing portion 118 that retains or holds one or more vials, ampoules, or the like, with three (3) vials 130a, 130b, and 130c shown. The housing portion 118 is at least partially pliable such that it can be squeezed together. The illustration of three (3) vials is arbitrary. Each vial 130a, 130b, 130c is made from a frangible material (e.g. glass) such that bending, twisting, squeezing or otherwise manipulating the vial causes the frangible vial to break or rupture. Each vial 130a, 130b, 130c holds an amount of sterile and/or filtered water (e.g. distilled water). Each vial 130a, 130b, 130c is sized to preferably, but not necessarily, hold approximately 5 ccs of water. Each vial 130a, 130b, 130c may also be sized to hold other and/or different amounts of water (or a single vial 130 of a size) preferably consistent with the size of the sponge 112 of the CAUTI inhibiting scrub 110 in order to wet and preferably, but not necessarily, saturate the sponge with water, and hydrate a dehydrated cleansing solution imbued in the sponge 112. Alternatively, the vials may hold the cleaning solution such that rupturing the vials serves to distribute the cleaning solution into the sponge.

As illustrated, the sponge 112 holds a dehydrated cleansing mixture of castile soap and tea tree oil, preferably, but not necessarily, in a 1:1 concentration. A source of castile soap and tea tree oil is Dr. Bronner's of Escondido, Calif. The cleansing mixture is preferably, but not necessarily, introduced into the sponge 112 when wet and allowed to dry. The amount of cleansing mixture is preferably, but not necessarily, correlated to the amount of water held in the vial(s) such that a 50-50 concentration of water and cleansing solution is created when the water is released from the vial(s) and allowed to soak into the sponge 112. The castile and tea tree oil soap is mild, non-irritating to the skin, eco-friendly and biodegradable. Catheter insertion site and perineal care can be accomplished frequently (e.g. daily) with minimal risk of irritation. The present cleansing mixture also provides minimal risk of breakdown of the normal vaginal floral in females.

Tea tree oil has been shown to inhibit cellular respiration in *E. Coli*, one of the most frequent bacteria to cause CAUTI, by disrupting the permeability barrier of the microbial membrane. The antibacterial effect of the tea tree oil is consistent to help prevent and/or inhibit infection from entering the body via the catheter insertion site. Testing of tea tree oil in a mixture with jojoba oil has also indicated the death of *Proteus Mirabilis, staphylococcus aureus*, and *pseudomonas aeruginosa*.

The CAUTI inhibiting scrub 110 further includes features for breaking or rupturing the frangible vials 130a, 130b, and 130c. Particularly, the housing 116 includes first and second compressible wings 120a, 120b. The wings 120a, 120b are formed to be a generally pliable plastic. The first wing 120a extends from one side of the rim 117 of the housing 116 while the second wing 120b extends from another side of the rim 117 opposite the first wing 120a. A first strut 121a extends from an inside surface of the first wing 120a to a side of the housing portion 118. The first strut 121a is preferably, but not necessarily, situated generally in a central or mid region of the first wing 120a and the housing portion 118. The second wing 120b extends from another side of the rim 117 of the housing 118 that is opposite the first wing 120a. A second and third strut 121b, 121c extend from an inside surface of the second wing 120b to another side of the housing portion 118 that is opposite the first wing 120a. The second and third struts 121b, 121c are positioned so as to straddle (be offset from) the first strut 121a. Thus, as the first and second wings 120a, 120b are pinched or squeezed together, the second and third struts 121b, 121c press against the housing portion 118 so as to bend the housing portion 118 about the first strut 121a. The bending causes the vials 130a, 130b, and 130c to rupture thereby releasing their contents (water) into the sponge 112. The wings 20a, 20b are shaped to allow a user to easily and firmly hold the scrub 10 both for rupturing the frangible vial 16 and for cleaning the desired area.

The present CAUTI inhibiting scrub 110 is sterile and thus preferably, but not necessarily individually packaged or wrapped as known in the art in order to keep the scrub 110 sterile before use. The method of use is essentially a two-step process. First, any wrapper is removed immediately prior to use. The user holds the scrub 110 by the wings 120a, 120b then squeezes the wings together. This causes the housing portion 118 surrounding/holding the frangible vials 130a, 130b, 130c to bend and thereby rupture or break the vials. The water within the vial is then dispensed into the body 112 to hydrate or rehydrate the dry or dehydrated cleansing mixture. The sponge 112 is now wet and sudsy/soapy with the water and cleansing mixture. The fingers 113 help disperse the cleansing mixture throughout the body 112 for thorough cleansing of the catheter insertion area and the perineal area.

It is to be understood that what has been described includes a novel method for inhibiting catheter associated urinary tract infections comprising providing a one time use absorbent body having first and second wings extending therefrom and at least one frangible vial containing a liquid; and squeezing the wings to release the liquid contents of the frangible vial into the absorbent body, thereby providing the absorbent body with a hydrated cleansing agent of castile soap and tea tree oil. The method may also include using the absorbent body to cleanse the catheter insertion area and the perineal area of a patient. The absorbent body may be provided with a dehydrated cleansing agent of castile soap and tea tree oil such that squeezing the wings releases water into the absorbent body to hydrate the cleansing agent. Alternatively or in addition, the cleansing agent of castile soap and tea tree oil may be contained in one or more of the frangible vial(s). The cleansing agent may be composed of a 1:1 mixture of the castile soap and tea tree oil.

What has also been described is a one time use cleansing device for inhibiting catheter associated urinary tract infections, comprising: an absorbent body; a plurality of fingerlings extending outwardly from a front side of the absorbent body; first and second wings extending from a back side of the absorbent body; and one or more liquid containing frangible vials disposed between the first and second wings such that squeezing the wings together causes the vials to rupture, thereby releasing the contents of the vials into the absorbent body; wherein at least one of the absorbent body and the one or more vials contain a cleansing agent of castile soap and tea tree oil. The one or more vials may contain the cleansing agent of castile soap and tea tree oil. Alternatively or in addition, the absorbent body may contain a dehydrated cleaning agent of castile soap and tea tree oil such that rupturing the vials releases water (or some other suitable liquid) into the absorbent body to hydrate the dehydrated cleansing agent. A debris filter may be disposed between the vials and the absorbent body. A housing may be situated on the debris filter and containing the one or more frangible vials. The first and second wings may be situated on opposite sides of the housing, the first wing connected to the housing by a first strut and the second wing connected to the housing by a second and third strut that are offset from the first strut. The cleansing agent may be composed of a 1:1 mixture of the castile soap and tea tree oil.

While the invention has been illustrated and described in detail in the foregoing drawings and description, the same is to be considered as illustrative and not restrictive in character, it being understood that only an illustrative embodiment thereof has been show and described and that all changes and modifications that are within the scope of the following claims are desired to be protected.

What is claimed is:

1. A method of cleaning a catheter insertion area and a perineal area of a patient comprising:
   providing a one-time use absorbent body having first and second wings extending therefrom and at least one frangible vial comprising a liquid, wherein at least one of the absorbent body and the frangible vial contain a cleansing agent of castile soap and tea tree oil;
   hydrating the absorbent body by squeezing the wings to release the liquid of the frangible vial onto the absorbent body; and
   using the hydrated absorbent body comprising said cleansing agent of castile soap and tea tree oil to cleanse the catheter insertion area and the perineal area of the patient.

2. The method of claim 1 in which the absorbent body is provided with a dehydrated cleansing agent of said castile soap and said tea tree oil and squeezing the wings releases water into the absorbent body to hydrate the cleansing agent.

3. The method of claim 1 in which the cleansing agent of castile soap and tea tree oil is contained in the frangible vial.

4. The method of claim 1 in which the cleansing agent is composed of a 1:1 mixture of the castile soap and tea tree oil.

5. A one-time use cleansing device comprising:
   an absorbent body;
   a plurality of fingerlings extending outwardly from a front side of the absorbent body;
   first and second wings extending from a back side of the absorbent body;
   one or more liquid containing frangible vials disposed between the first and second wings such that squeezing the wings together causes the vials to rupture, thereby releasing the liquid from the vials into the absorbent body;
   wherein at least one of the absorbent body and the one or more vials contain a cleansing agent of castile soap and tea tree oil.

6. The cleansing device of claim 5 in which the one or more vials contain the cleansing agent of castile soap and tea tree oil.

7. The cleaning device of claim 5 in which the absorbent body contains a dehydrated cleaning agent of said castile soap and said tea tree oil and rupturing the vials releases water into the absorbent body to hydrate the dehydrated cleansing agent.

8. The cleaning device of claim 5 further comprising a debris filter disposed between the vials and the absorbent body.

9. The cleaning device of claim 8 further comprising a housing situated on the debris filter and containing the one or more frangible vials.

10. The cleaning device of claim 9 in which the first and second wings are situated on opposite sides of the housing, the first wing connected to the housing by a first strut and the second wing connected to the housing by a second and third strut that are offset from the first strut.

11. The cleaning device claim 10 in which the cleansing agent is composed of a 1:1 mixture of the castile soap and tea tree oil.

* * * * *